United States Patent [19]
Peterson

[11] Patent Number: 6,004,303
[45] Date of Patent: Dec. 21, 1999

[54] CHOKER CATHETER

[75] Inventor: Francis C Peterson, Prescott, Wis.

[73] Assignee: Phillips Plastics Corporation, Phillips, Wis.

[21] Appl. No.: 08/988,157

[22] Filed: Dec. 10, 1997

[51] Int. Cl.$^6$ .......................... A61M 5/00; A61M 5/178
[52] U.S. Cl. .......................................... 604/264; 604/167
[58] Field of Search ................................ 604/264, 164, 604/167, 272, 280, 256; 137/846, 853; 251/149

[56] References Cited

U.S. PATENT DOCUMENTS

| | | | |
|---|---|---|---|
| 4,760,933 | 8/1988 | Christner et al. | 220/86 R |
| 4,828,554 | 5/1989 | Griffin | 604/350 |
| 5,127,626 | 7/1992 | Hilal et al. | . |
| 5,158,553 | 10/1992 | Berry et al. | 604/248 |
| 5,330,437 | 7/1994 | Durman | 604/167 |
| 5,364,372 | 11/1994 | Danks et al. | . |
| 5,538,509 | 7/1996 | Dunlap et al. | . |
| 5,545,150 | 8/1996 | Danks et al. | . |
| 5,580,344 | 12/1996 | Hasson | . |
| 5,634,937 | 6/1997 | Mollenauer et al. | . |
| 5,720,730 | 2/1998 | Blake, III | 604/167 |

FOREIGN PATENT DOCUMENTS

| | | |
|---|---|---|
| 2275420 | 8/1994 | United Kingdom . |
| WO 94/22357 | 10/1994 | WIPO . |

*Primary Examiner*—Corrine McDermott
*Assistant Examiner*—Michael J. Hayes

[57] ABSTRACT

The present invention is directed to an apparatus for use in internal surgical procedures, more particularly, an apparatus for use in laparoscopic surgical procedures providing a simple and cost effective sealing mechanism within a cannula which readily accepts the repeated insertion and removal of surgical instruments through the seal without permitting escape of gasses through the seal. In one particular embodiment, the apparatus consists of a rigid tube having an inner surface defining a hollow channel and a flexible sleeve located within the hollow channel forming an inner channel within the hollow channel where the flexible sleeve is sufficiently elastic to close the inner channel in response to pressurization between the outside of the flexible sleeve and the inner surface of the hollow channel. The flexible sleeve is also constructed and arranged to permit an external instrument to pass through the inner channel of the sleeve while maintaining the air channel closed due to the pressurization between the sleeve and the inner surface of a hollow channel.

12 Claims, 3 Drawing Sheets

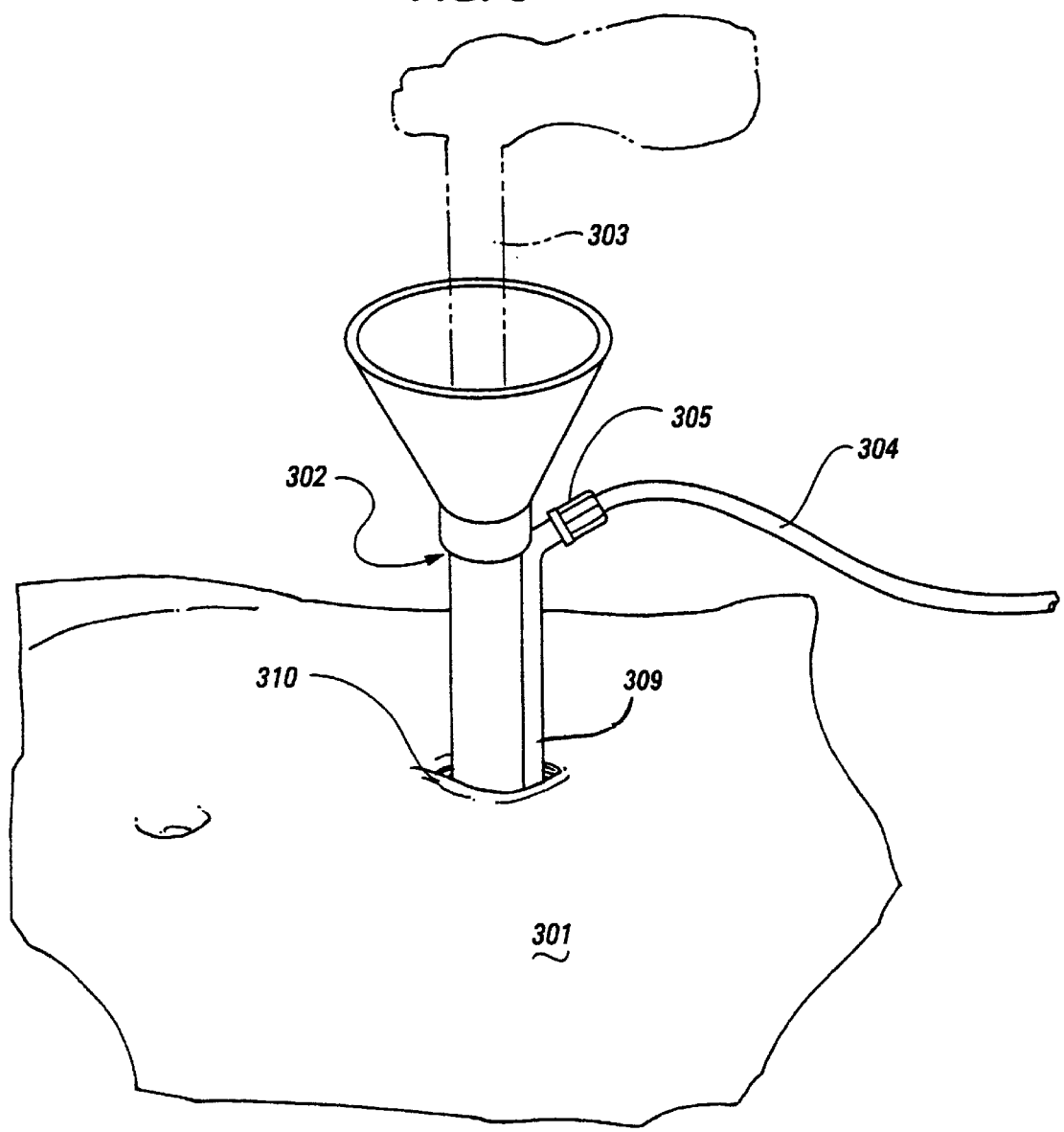

CHOKER CATHETER

FIELD OF THE INVENTION

The present invention relates to an apparatus for use in laparoscopic surgery and, more particularly, to an apparatus for providing a seal or valve structure within a cannula which effectively and cost efficiently provides a means for preventing an inert gas from escaping while allowing the repeated insertion and removal of surgical instruments through the cannula.

BACKGROUND OF THE INVENTION

Surgical techniques and instruments have been developed which, among other things, reduce the size of incisions required to perform various surgical procedures. These techniques and instruments have been successful to various degrees. Indeed, surgical procedures which only a few years ago required an incision six or seven inches in length are today performed through incisions requiring less than one inch in length.

Trocars are one type of surgical instrument which have significantly contributed to these advances. In general, trocars are sharp pointed surgical instruments which can be used to create and maintain small, bowl like incisions in a body cavity. Surgical instruments, including miniaturized optical devices, can be inserted through these small incisions and manipulated to perform surgical procedures within the body cavity without ever exposing the patient's internal organs or structures to the outside environment. Thus, by enabling the creation and maintenance of small working holes within a patient's body wall, conventional trocars have greatly contributed to the reduction and size of the incisions required to perform surgical procedures and reduce the related complications.

Conventional trocars generally include an obturator and a cannula. An obturator is a small, nail like structure for penetrating the body wall to create a working channel into the body cavity. The cannula is a tube like structure which is inserted into the incision made by obturator to maintain a working channel even after the obturator is removed. In a typical scenario, the obturator and cannula are assembled into a single unit by inserting the obturator within the cannula and then a combination is used to puncture the body wall. The obturator can then be carefully withdrawn from the cannula without removing the cannula from the body wall. Surgical instruments can be inserted through this cannula to perform an entire surgical procedure within the body cavity as mentioned above.

In many surgical procedures involving trocars, the body cavity is inflated with a non toxic gas before the trocar is employed to create a working pocket or volume within the patient and to prevent the trocar from penetrating internal organs during insertion. For example in an appendectomy, a patient's abdomen is inflated with a gas through a veress needle. The obturator is then used to place cannulas in various locations throughout the inflated abdomen to perform the procedure. One such cannula would typically be used to pass a small camera and light into the body cavity so the surgeon could view the operating area within the patient. Other cannulas would be used at other locations to pass surgical instruments into the cavity and remove tissue such as the appendix from the patient.

It is important to maintain the abdomen of the patient in an inflated state throughout this procedure. To this end, conventional cannulas are often provided with the sealing flap valves or the like which prevent the gas from escaping from the patient's abdomen after the obturator has been withdrawn. However these sealing valves do not prevent gas leakage when surgical instruments having a diameter which is smaller than the diameter of the cannula is employed. Instead gas can easily pass through the gap between the inner walls of the cannula and the outer surface of the surgical instrument to deflate the work area. To prevent such deflation of this type from occurring, physicians often are required to utilize only those instruments whose dimensions closely match those of the cannula. This requirement apparently limits the surgeon's freedom of choice in selecting surgical instruments for the procedure. Thus, while a surgeon's instrument might be preferred by a physician, the physician might nonetheless be forced to use a less preferred, and possibly less effective, tool to perform a procedure to avoid deflating a body cavity.

SUMMARY OF THE INVENTION

The present invention is directed to an apparatus for use in internal surgical procedures, more particularly, an apparatus for use in laparoscopic surgical procedures providing a simple and cost effective sealing mechanism within a cannula which readily accepts the repeated insertion and removal of surgical instruments through the seal without permitting escape of gasses through the seal. In one particular example, the apparatus consists of a rigid tube having an inner surface defining a hollow channel and a flexible sleeve located within the hollow channel forming an inner channel within the hollow channel where the flexible sleeve is sufficiently elastic to close the inner channel in response to pressurization between the outside of the flexible sleeve and the inner surface of the hollow channel. The flexible sleeve is also constructed and arranged to permit an external instrument to pass through the inner channel of the sleeve while maintaining the inner channel closed due to the pressurization between the sleeve and the inner surface of a hollow channel.

The above summary of the present invention is not intended to describe each illustrated embodiment or every limitation of the present invention. The figures in the detailed description which follow more particularly exemplify these embodiments.

BRIEF DESCRIPTION OF THE DRAWINGS

In invention may be more completely understood in consideration of the detailed description of various embodiments of the invention which follow in connection with the accompanying drawings, in which:

FIG. 3 is a diagram according to the present invention showing how surgical instruments can be inserted through the cannula and its inner seal while still maintaining a closed seal within the cannula.

Figure 1:
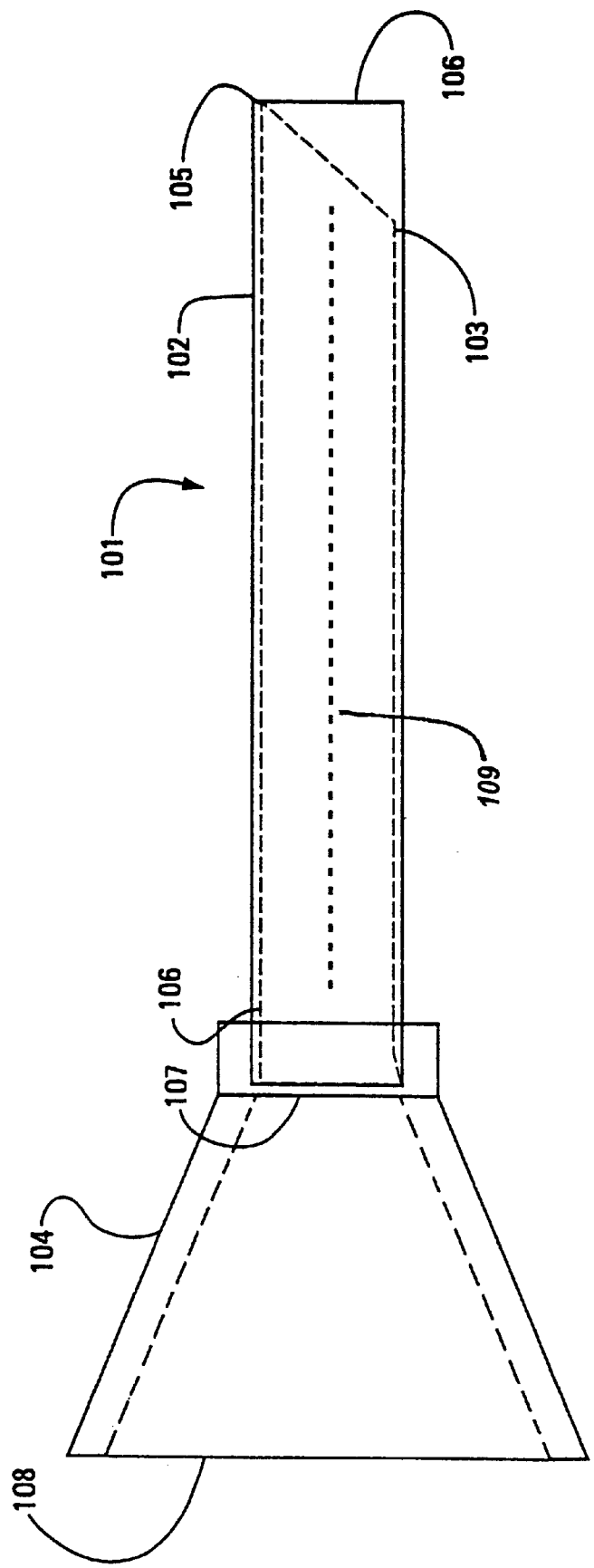
FIG. 1 is a side view according to the present invention including the outer cannula and the inner seal.

While the invention is amenable to other various modifications in alternative forms, specifics thereof have been shown by way of example in the drawings and will be described in detail. It should be understood, however, that the intention is not to limit the invention to a particular embodiment described. On the contrary, the intention is to cover all modifications, equivalents, and alternatives falling within the spirit and scope of the invention as defined by the appended claims.

DETAILED DESCRIPTION

The present invention in believed to be applicable to a variety of apparatus and arrangements in which external instruments are to be passed through an opening separating two environments in which a pressure difference between these environments exists and in which a seal between these environments needs to be maintained. The invention has been found to be particularly advantageous in application environments in which laparoscopic surgery is performed and in which surgical instruments are to be passed into a body cavity to perform an operation. While the present invention is not so limited, an appreciation of various aspects of the invention is best gained through discussion of application examples operating in such a laparoscopic surgical environment. The present invention, is of course, applicable to providing an apparatus that permits any external instruments to be passed between two environments sealed to maintain the pressure difference between the two environments.

Referring to FIG. 1, the surgical instrument 101 consists of an elongated rigid tube 102 in which a flexible tube or sleeve 103 is placed within a hollow channel located within the rigid tube 102. The flexible tube or sleeve 103 is supported on the rigid tube 102 using a weld 105 attaching the bottom of the tube 102 to the side wall. The flexible tube 103 is also supported with some overlap at the point at which the rigid tube mates with an entrance receptacle 104 as it attaches to the second end of the rigid tube 107. The receptacle is a funnel shaped device which has a wide opening 108 and a narrow opening 107 in which its narrow opening 107 mates with the size of the second end of the rigid tube 102. This funnel structure is useful in guiding the insertion of external instruments into the rigid tube 102 and flexible tube 103 by permitting the funnel structure to guide the instruments towards the center of the rigid and flexible tubes.

A flexible tube 103 is constructed of a slippery polyurethane or Teflon-like material to permit the easy passage of an external instrument through the sleeve to exit the rigid tube 102 at its first end 106. The flexible tube 103 use of a slippery, plastic, polyurethane-like material provides the required elasticity to allow the flexible tube to be compressed under pressure to close the opening of the inner channel formed within the flexible tube 103. In one example embodiment, the flexible tube 103 runs along an axial line 109 within the rigid tube 102.

When in use for laparoscopic surgery, the rigid tube 102 is inserted within a small hole within the body cavity which can be sized to match the outer diameter of the rigid tube 102. The body cavity is generally pressurized using an inert gas, such as $CO_2$, such that the internal pressure within the body cavity is greater than the outside air. As such, when the rigid tube 102 is inserted within the pressurized body cavity, this pressurization enters the rigid tube at its first end 106 compressing the flexible tube 103 upwards. Because the flexible tube 103 is attached at the weld 105, the flexible tube 103 gathers and compresses, closing the opening of the inner channel thus preventing the escape of the pressurized gas from inside the body cavity.

When in this configuration, a surgical instrument can be inserted through receptacle 104, as it is passed through the opening of receptacle 108 to the mating surfaces of rigid tube's second end and the receptacle 107, to enter within the inner channel of the now collapsed flexible tube 103. As the instrument is inserted through the flexible tube, the flexible tube will deform around the external instrument, thus permitting the instrument to pass through both the flexible tube 103 and exit the rigid tube 102. At the same time, the pressurization is present within the rigid tube's first end 106. The pressurization continues to press the flexible tube against the surfaces of the external instrument as it passes through the inner channel, thus maintaining a pressure within the inner channel. The external instrument can now be used to perform surgical procedures within the body cavity.

As the external instrument is removed, it passes back through the inner channel of the flexible tube. Pressurization from within the body cavity maintains the collapsed structure of the flexible tube, thus maintaining the seal of the inner channel around the instrument until it is closed when the instrument is completely removed.

Figure 2:
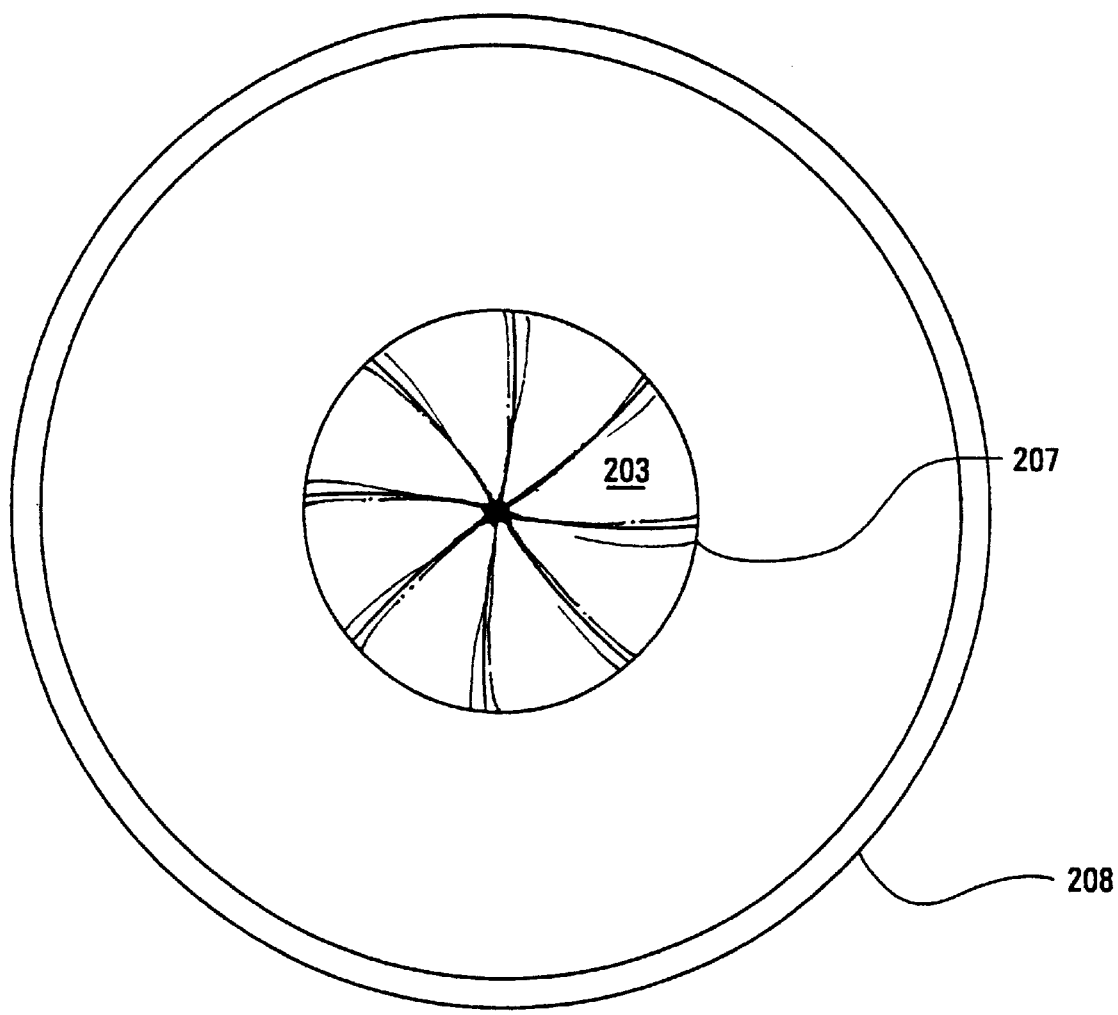
FIG. 2 is an end view according to the present invention of the cannula with its inner seal.

Referring to FIG. 2, an end view of the surgical instrument looking down towards the top of the receptacle is shown. The outer edge 208 shows the outer dimension of the receptacle which funnels down towards the mating surface between the receptacle and the rigid tube at 207. The flexible tube is depicted in its closed position 203 as the flexible tube is gathered up to close the opening within the inner channel formed within 207. An external instrument would be inserted down through the center of the structure as the flexible tube 203 conforms to the shape and surface of this external instrument as it passes down through the length of the inner channel formed within the rigid and flexible tubes.

Referring to FIG. 3, an embodiment of the present invention is shown in use where the cannula 302 is inserted within a body cavity 301 at an incision 310. A surgical instrument 303 is passed through the center of cannula 302 again through the inner channel of the flexible tube which seals the opening through the cannula. In this particular embodiment, an additional structure has been added which permits the supply of an inert gas to be placed within the body cavity 301. This additional structure consists of an inert gas line 304 which comes from an external source connected to a valve structure 305 which allows the gas supply to be turned on and off. This valve structure can be made part of the receptacle housing. This structure is also connected to a secondary tube 309 which runs parallel to the rigid tube 102 of the cannula 302 with an opening near at the first end of the rigid tube 102 permitting the gas to enter within the body cavity 301 on the far end side of the flexible tube 103, providing the pressurization within the body cavity needed to close the inner channel of the flexible tube 103. This supply of gas can be made part of the cannula 302 as described herein or can be made as a separate structure inserted in the body at some other location.

The above specification, examples and data provide a complete description of the manufacture and use of the composition of the invention. Since many embodiments of the invention can be made without departing from the spirit and scope of the invention, the invention resides in the claims hereinafter appended.

I claim:

1. An apparatus for use in internal surgical procedures, comprising:

an elongated member having at least one inner surface defining a hollow channel and having an insertion end adapted for insertion through a hole in a body wall and into a body cavity; and a flexible sleeve secured adjacent a first location and a second distal location within the hollow channel, the second distal location being adjacent the insertion end, and the flexible sleeve having a sleeve end adjacent the insertion end at least one inner surface forming an inner channel, the sleeve end unsecured around a majority of the hollow channel, the flexible sleeve being sufficiently elastic to close the inner channel in response to pressurization introduced within the body cavity adjacent the insertion end between an area outside the sleeve and said at least one inner surface of the elongated member.

2. An apparatus, according to claim 1, wherein the flexible sleeve includes at least one wall constructed and arranged to permit an external instrument to pass through the inner channel while maintaining the inner channel closed due to said pressurization between the sleeve and said at least one inner surface.

3. An apparatus for use in laparoscopic surgical procedures, comprising:

an elongated rigid member containing a hollow channel having at least one opening and an insertion end adapted for insertion through a hole in a body wall and into a body cavity;

a receptacle having a first end attached near one end of the rigid member; and a flexible sleeve having an inner channel, having a sleeve end adjacent the insertion end, located within the hollow channel of the rigid member, and being supported via the rigid member at first and second distal locations along the length of the member, the second distal location being along the insertion end and the sleeve end unsecured around a majority of the hollow channel, and wherein the flexible sleeve is configured and arranged between the first location and second location such that the sleeve is compressed in response to pressure introduced within the body cavity by pressure in the body cavity to completely close the opening.

4. An apparatus, according to claim 3, wherein the flexible sleeve includes at least one wall constructed and arranged to permit an external instrument to pass through the inner channel while maintaining the inner channel closed due to said pressurization between the sleeve and the elongated rigid member.

5. An apparatus for use in laparoscopic surgical procedures, comprising:

an elongated rigid tube containing a hollow channel having at least one opening and an insertion end adapted for insertion through a body wall and into a body cavity;

a receptacle having a first end attached to a first end of the rigid lube; and a flexible sleeve located within the hollow channel of the rigid tube and being secured via the rigid tube at a first location and a distal second location proximate the insertion end, the flexible sleeve having a sleeve end located adjacent the insertion end and the sleeve end being unsecured around a majority of the hollow channel, wherein the flexible sleeve is configured and arranged to collapse between the first and second location, and to receive pressure applied to the insertion end within the body cavity such that the sleeve collapses when under the pressure applied to the insertion end while in use to completely close the opening.

6. An apparatus, according to claim 5, wherein the flexible sleeve is constructed and arranged to include an inner channel and to permit an external instrument to pass through the inner channel while maintaining the inner channel closed due to said pressurization between the sleeve and the rigid tube.

7. An apparatus for use in internal surgical procedures, comprising:

an elongated member defining a hollow channel; and a flexible sleeve secured adjacent distal first and second ends of the member within the hollow channel, and having at least one inner surface forming an inner channel, the flexible sleeve being configured and arranged to close the inner channel in response to pressurization introduced between an area outside the sleeve and said at least one inner surface of the member.

8. A valve for use in sealing an opening within a cannula during use in laparoscopic surgical procedures, comprising:

an elongated rigid tube containing a hollow channel running from a first end of the tube to a distal insertion end of the tube, the insertion end of the tube adapted for insertion through a body hole and into a body cavity;

a receiving means having a narrow end, a wide end, and a tapered channel running from the wide end to the narrow end of the receptacle, wherein the narrow end of the receptacle is attached to the first end of the tube such that the hollow channel of the tube engages the tapered channel of the receptacle to form an opening; and a flexible sleeve, including a sleeve end adjacent the insertion end, located within the hollow channel of the rigid tube and being attached to the rigid tube at the first end of the tube and attached along the distal insertion end of the tube, the sleeve end being unsecured around a majority of the hollow channel such that the sleeve is compressed and closed in response to pressure introduced at the distal insertion end of the elongated rigid tube.

9. A method for use in internal surgical procedures, comprising:

providing an apparatus including an elongated member defining a hollow channel, and a flexible sleeve secured adjacent a first end and a second distal end of the member within the hollow channel, the flexible sleeve having at least one inner surface forming an inner channel and having a sleeve end adjacent the distal end, the sleeve end being unsecured around a majority of the hollow channel;

inserting a portion of the elongated member through a body wall and into a body cavity, the portion including the second end; and introducing pressure through said portion and between an area outside the sleeve and said at least one inner surface of the member the flexible sleeve and causing the flexible sleeve to close the inner channel.

10. A method for use in internal surgical procedures, according to claim 9, further including inserting a surgical tool into the inner channel.

11. A method for use in internal surgical procedures, according to claim 9, wherein introducing pressure causes the flexible sleeve to close the inner channel around the surgical tool.

12. A method for use in internal surgical procedures, according to claim 9, further including using an upper end of the apparatus to guide the surgical tool.

* * * * *

UNITED STATES PATENT AND TRADEMARK OFFICE
CERTIFICATE OF CORRECTION

PATENT NO. : 6,004,303
DATED : December 21, 1999
INVENTOR(S) : Peterson

It is certified that error appears in the above-identified patent and that said Letters Patent is hereby corrected as shown below:

Col. 2, line 46: "In invention" should read --The invention--.

Col. 3, line 3, "in" should read --is--.

Signed and Sealed this

Twenty-seventh Day of March, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO. : 6,004,303
DATED : December 21, 1999
INVENTOR(S) : Francis C. Peterson It is certified that error appears in the above-identified patent and that said Letters Patent is hereby corrected as shown below:

Column 6,
Claim 7 should be deleted.

Signed and Sealed this

Twenty-seventh Day of April, 2004

JON W. DUDAS
*Acting Director of the United States Patent and Trademark Office*